(12) United States Patent
Kaufman et al.

(10) Patent No.: US 8,961,569 B2
(45) Date of Patent: Feb. 24, 2015

(54) LOCKING PEDICLE SCREW DEVICES, METHODS, AND SYSTEMS

(75) Inventors: Kevin Kaufman, Fort Worth, TX (US); John Stokes, Austin, TX (US); Robert Josey, Austin, TX (US); Bernard Guiot, Denver, CO (US); Joshua Kaufmann, Austin, TX (US); Scott Bryant, Austin, TX (US); Greg Calbert, Austin, TX (US)

(73) Assignee: Genesys Spine, Austin, TX (US)

( * ) Notice: Subject to any disclaimer, the term of this patent is extended or adjusted under 35 U.S.C. 154(b) by 738 days.

(21) Appl. No.: 12/897,525

(22) Filed: Oct. 4, 2010

(65) Prior Publication Data
US 2012/0083850 A1 Apr. 5, 2012

(51) Int. Cl.
*A61B 17/70* (2006.01)
*A61B 19/00* (2006.01)

(52) U.S. Cl.
CPC ........... *A61B 17/7032* (2013.01); *A61B 17/701* (2013.01); *A61B 17/7037* (2013.01); *A61B 2019/307* (2013.01)
USPC ...................................................... 606/272

(58) Field of Classification Search
CPC ................... A61B 17/7032; A61B 17/7037
USPC ......... 606/264–270, 272–274, 305–308, 319, 606/328, 290–291, 54–59, 324; 411/393, 411/149; 403/362
See application file for complete search history.

(56) References Cited

U.S. PATENT DOCUMENTS

| | | | | |
|---|---|---|---|---|
| 4,034,788 A | * | 7/1977 | Melone | 411/134 |
| 5,080,545 A | * | 1/1992 | McKinlay | 411/149 |
| 5,207,678 A | | 5/1993 | Harms et al. | |
| 5,474,555 A | | 12/1995 | Puno et al. | |
| 5,662,651 A | * | 9/1997 | Tornier et al. | 606/60 |
| 5,690,630 A | * | 11/1997 | Errico et al. | 606/264 |
| 6,896,465 B2 | * | 5/2005 | Andersson | 411/533 |
| 7,081,117 B2 | | 7/2006 | Bono et al. | |
| 7,125,426 B2 | | 10/2006 | Moumene et al. | |
| 7,588,571 B2 | * | 9/2009 | Olsen | 606/57 |
| 7,625,394 B2 | * | 12/2009 | Molz et al. | 606/270 |
| 7,678,139 B2 | | 3/2010 | Garamszegi et al. | |
| 7,914,559 B2 | * | 3/2011 | Carls et al. | 606/270 |

(Continued)

FOREIGN PATENT DOCUMENTS

| | | |
|---|---|---|
| EP | 1 949 864 | 7/2008 |
| WO | WO 2006047555 | 5/2006 |
| WO | WO 2009114799 | 9/2009 |

OTHER PUBLICATIONS

Wikipedia, Encyclopedia entry for "Detent," dated Jul. 15, 2010, pp. 1-2.

(Continued)

*Primary Examiner* — Jan Christopher Merene
*Assistant Examiner* — Atiya Mahmud
(74) *Attorney, Agent, or Firm* — Trop, Pruner & Hu, P.C.

(57) ABSTRACT

An embodiment of the invention provides for a pedicle screw system including a bone anchor, linkage rod, tulip, set screw, and detent plate. When the set screw is fully tightened against the detent plate, pluralities of ridges on opposing faces of the detent plate and set screw cooperate by providing catches to prevent unwanted loosening of the set screw, which could lead to unwanted rod slippage and instability in the orthopedic fixation unit.

14 Claims, 8 Drawing Sheets

(56) References Cited

U.S. PATENT DOCUMENTS

| | | | |
|---|---|---|---|
| 8,062,340 B2 * | 11/2011 | Berrevoets et al. | 606/270 |
| 2005/0033296 A1 | 2/2005 | Bono et al. | |
| 2005/0177154 A1 | 8/2005 | Moumene et al. | |
| 2005/0207865 A1 * | 9/2005 | Disantis et al. | 411/160 |
| 2005/0240180 A1 * | 10/2005 | Vienney et al. | 606/61 |
| 2005/0286988 A1 * | 12/2005 | Harris | 411/149 |
| 2006/0161152 A1 | 7/2006 | Ensign et al. | |
| 2006/0287652 A1 * | 12/2006 | Lessig et al. | 606/54 |
| 2009/0105716 A1 | 4/2009 | Barrus | |
| 2010/0174325 A1 | 7/2010 | Won et al. | |
| 2010/0312287 A1 * | 12/2010 | Jackson | 606/302 |
| 2011/0178559 A1 * | 7/2011 | Barry | 606/302 |

OTHER PUBLICATIONS

Wikipedia, Encyclopedia entry for "Set screw," dated Jul. 15, 2010, pp. 1-2.
GENESYS TiLOCK PSS, "TiLock Pedicle Screw System Surgical Technique," 2010, pp. 1-6.
Allez Spine, "The Laguna Pedicle Screw System Surgical Technique Guide," date unknown, pp. 1-29.

* cited by examiner

LOCKING PEDICLE SCREW DEVICES, METHODS, AND SYSTEMS

BACKGROUND

Spinal fixation devices can be used to provide, for example, immobilization and stabilization of spinal segments in patients (e.g., humans, dogs, cats, and other animals). Fixation devices may be used to help fuse bone segments (e.g., vertebrae) in the treatment of instabilities or deformities of, for example, the cervical, thoracic, lumbar, and/or sacral spine. Such instabilities or deformities may include, for example, degenerative disc disease (DDD); spondylolisthesis; trauma (i.e., fracture or dislocation); spinal stenosis; curvatures (i.e., scoliosis, kyphosis, and/or lordosis); tumor; pseudoarthrosis; and failed previous fusions.

However, there are risks associated with such fixation devices. Such risks include, for example, device component fracture, loss of fixation through connecting rod slippage, non-union, fracture of the vertebra, neurological injury, and vascular or visceral injury. For example, internal fixation appliances are load sharing devices used to obtain bone alignment until normal healing occurs. Thus, implants can break and/or connecting rods can slip when fixation systems are subjected to loading associated with, for example, normal patient movements, delayed union, or non-union situations. The degree or success of union, loads produced by weight bearing, and activity levels will, among other conditions, dictate the longevity of the implant. Robust fixation systems are needed to lessen risks associated with fixation and to promote better outcomes for patients.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical contact with each other and "coupled" may mean that two or more elements co-operate or interact with each other, but they may or may not be in direct physical contact.

An embodiment of the invention provides for a pedicle screw system including a bone anchor, linkage rod, tulip, set screw, and detent plate. When the set screw is fully tightened against the detent plate (thereby compressing the rod within the tulip), pluralities of ridges on opposing faces of the detent plate and set screw cooperate by abutting each other in a resistive manner to prevent unwanted loosening of the set screw, which could lead to unwanted rod slippage and instability in the orthopedic fixation unit.

FIGS. 1-9 address various methods, embodiments, and perspectives of orthopedic linkage securing anchor assemblies.

Figure 1:
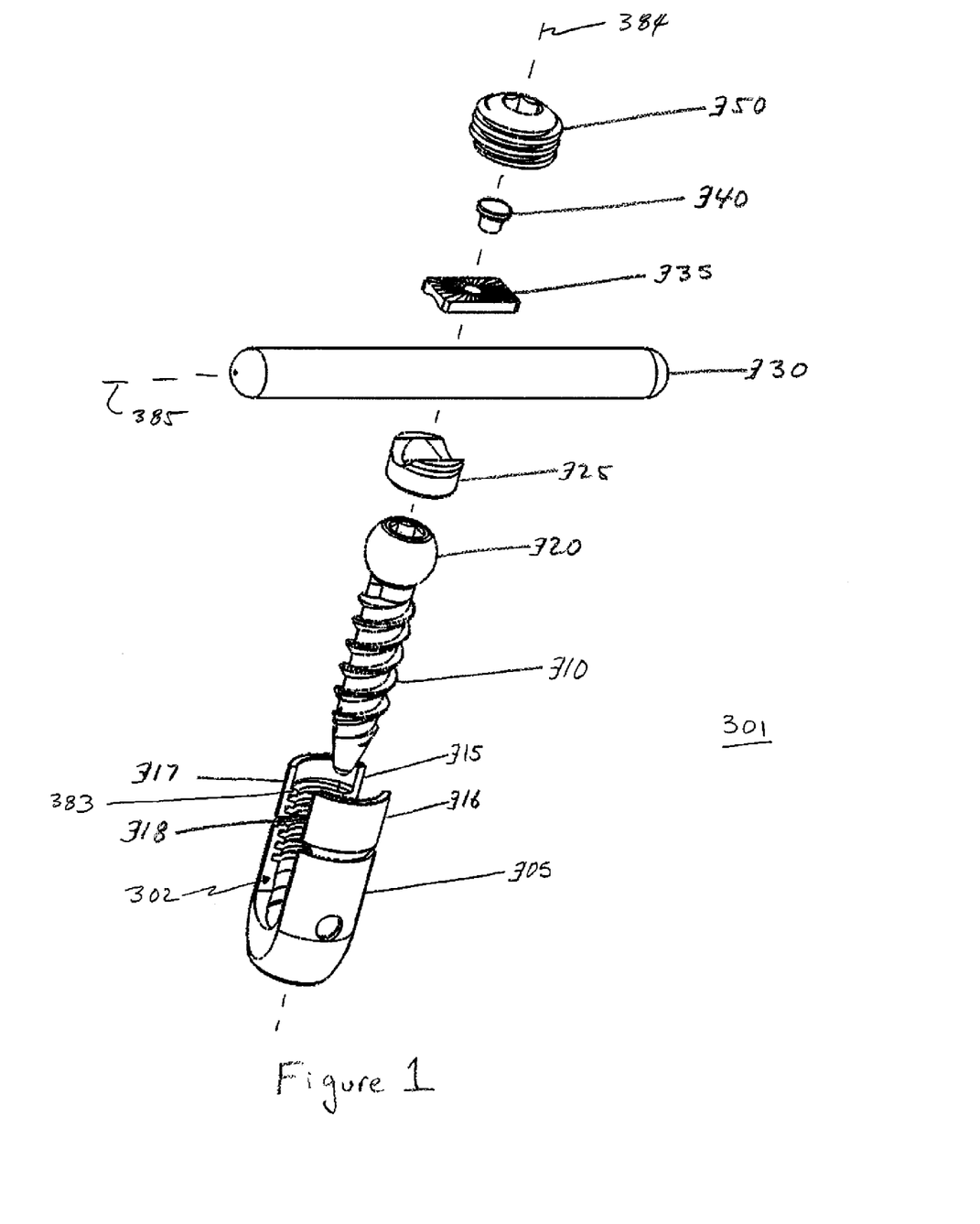
FIG. 1 includes an assembly in an embodiment of the invention.

In FIG. 1 anchor assembly 301 includes an anchor element 310 to attach to a bone. Element 310 may include a bone screw but is not so limited and may include nails, pins, and the like. Assembly 301 further includes tulip 305, which couples to anchor element 310. Tulip 305 includes open slot 302 to receive linkage 330. The linkage may include a rod for intervertebral fusion or fixation but is not so limited and may include wires, plates, and the like. Tulip 305 may include side walls defined by side wall edges 315, 316, 317, 318, which cooperate to define at least a portion of open slot 302. Assembly 301 further includes detent plate 335 to couple to linkage 330 and reside, at least partially, between the side walls of tulip 305. In an embodiment detent plate 335 resides directly between respective opposing side wall edges 317, 318 and/or 315, 316.

Figures 2, 9:
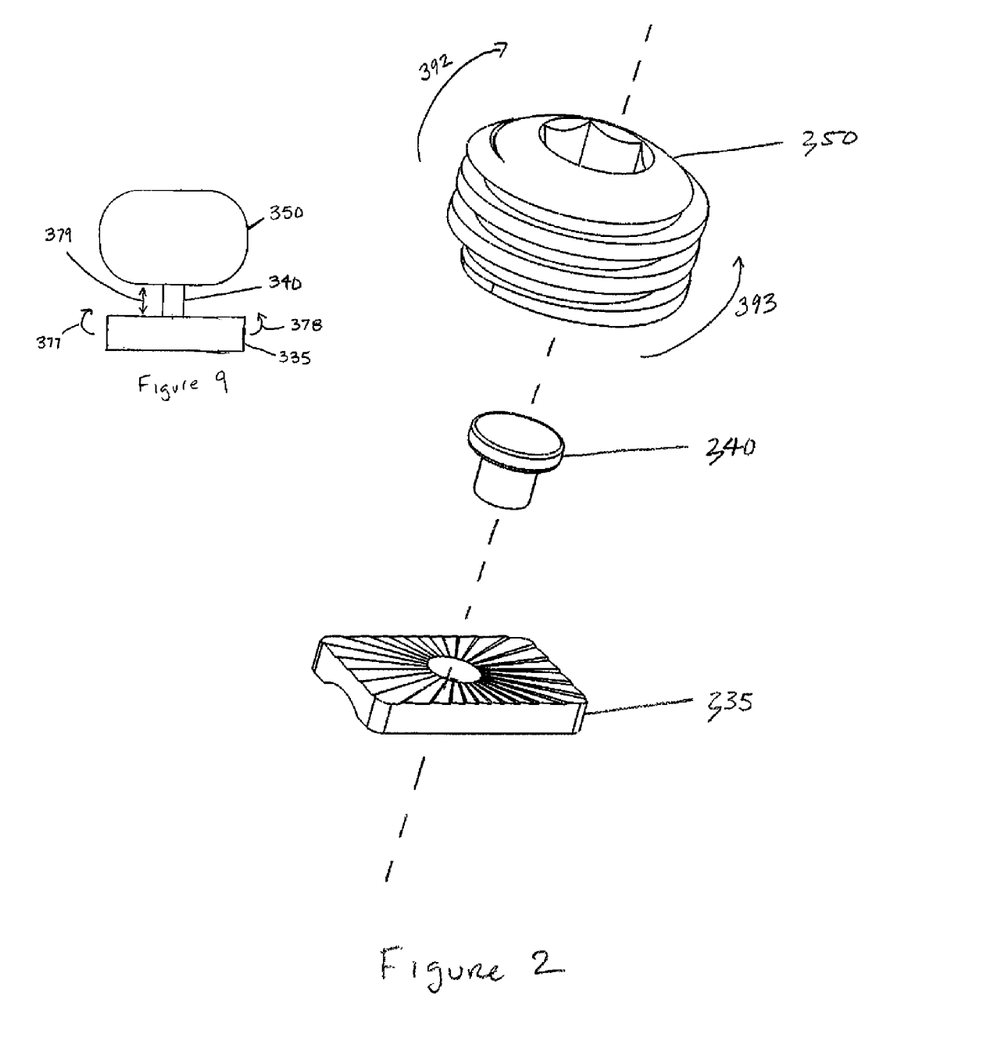
FIG. 2 includes a set screw, pivot, and detent plate in an embodiment of the invention.
FIG. 9 includes an assembly in an embodiment of the invention.
Figure 3A:
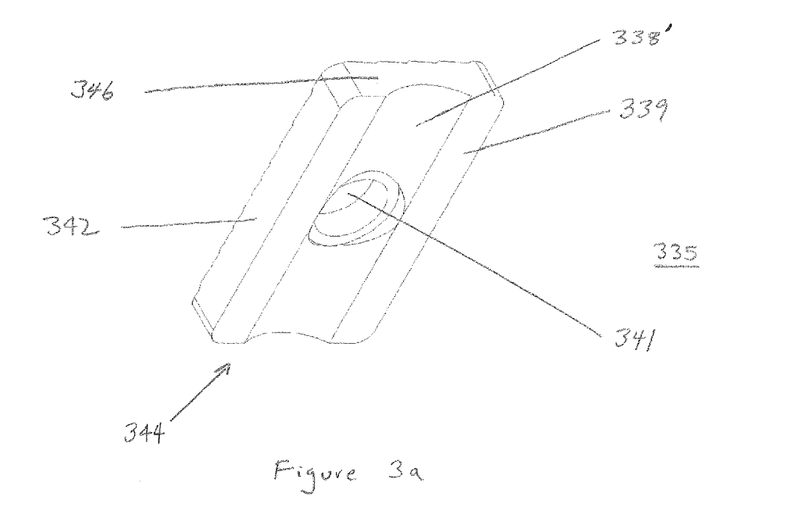
FIGS. 3a and 3b include different perspectives of a detent plate in an embodiment of the invention.
Figure 3B:
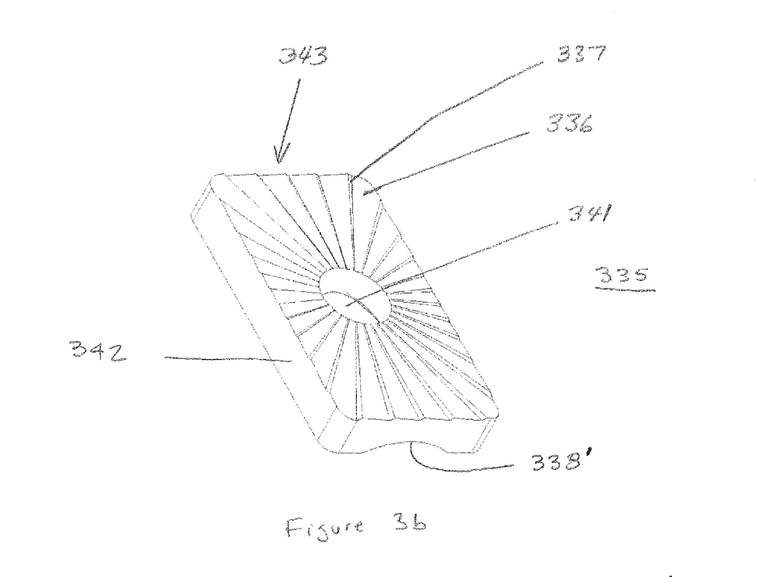
Figure 4A:
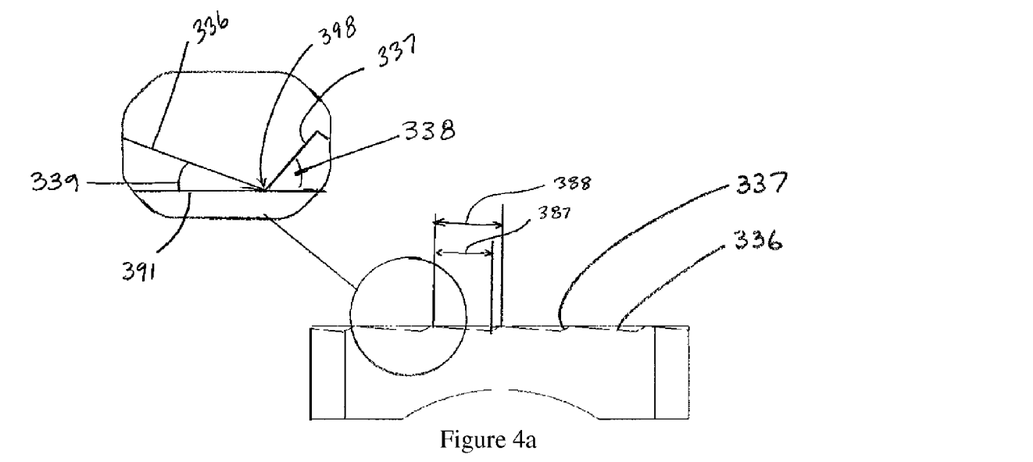
FIG. 4a includes a side view of a detent plate and FIG. 4b includes a top view of the detent plate in an embodiment of the invention.
Figure 4B:
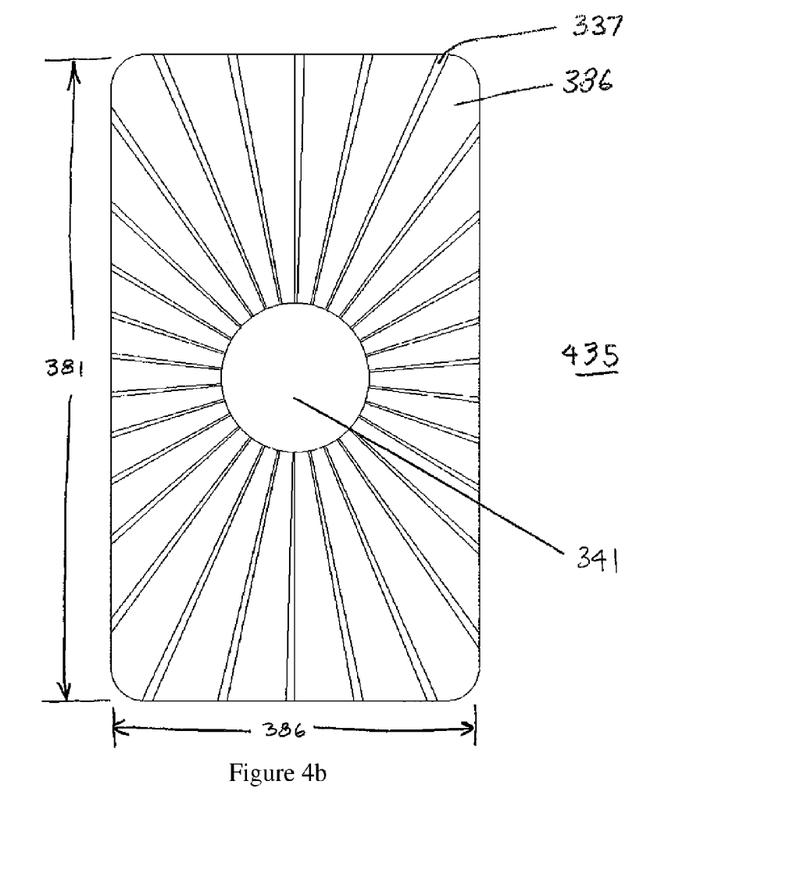

As seen in FIGS. 2-4, detent plate 335 has superior detent face 343 including a radially disposed plurality of ridges. One particular representative ridge is discussed for purposes of simplicity. To that end, one such ridge includes resist face 337 formed at acute angle 338 with respect to superior detent face plane 391. The ridge further includes advance face 336 formed at acute angle 339 with respect to superior detent face plane 391. As used herein, an acute angle has a measure of less than 90°. Angle 339 is "smaller" and "flatter" than angle 338. In other words, the resist face is more steeply inclined than the advance face. The flatness of angle 339 and face 336 provides for relatively easier advancement of set screw 350 across detent plate 335 during initial set screw 350 tightening. The steepness of angle 338 and face 337 provides for relatively difficult loosening of set screw 350 across detent plate 335 to help preclude or limit unwanted set screw loosening. In an embodiment, tip-to-tip distance 388 may be generally 0.5, 0.6, 0.7, 0.8, 0.9, 1.0, 1.1, 1.2, 1.3, 1.4, 1.5 mm and the like and tip-to-trough distance 387 may be generally 0.5, 0.6, 0.7, 0.8, 0.9, 1.0, 1.1, 1.2, 1.3, 1.4, 1.5 mm and the like. Also, in an embodiment advance face 336 is flatter and bigger in total surface area than resist face 337 and advance face 356 is flatter and bigger in total surface area than resist face 357. This may be seen based on length 388 as opposed to the differential in lengths 387 and 388. The differential in surfaces areas is also readily seen in FIGS. 4 (top view of detent plate) and 6 (top view of set screw).

Figure 5A:
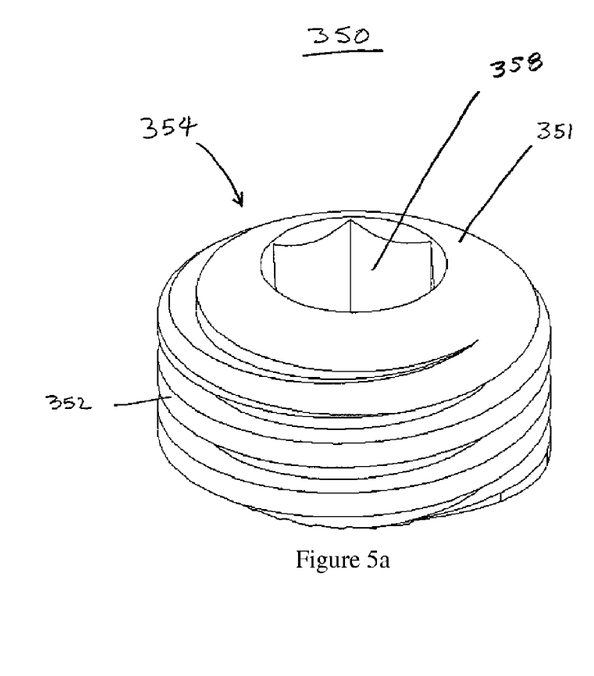
FIG. 5a includes a perspective view of a set screw and FIG. 5b includes a side view of the set screw in an embodiment of the invention.
Figure 5B:
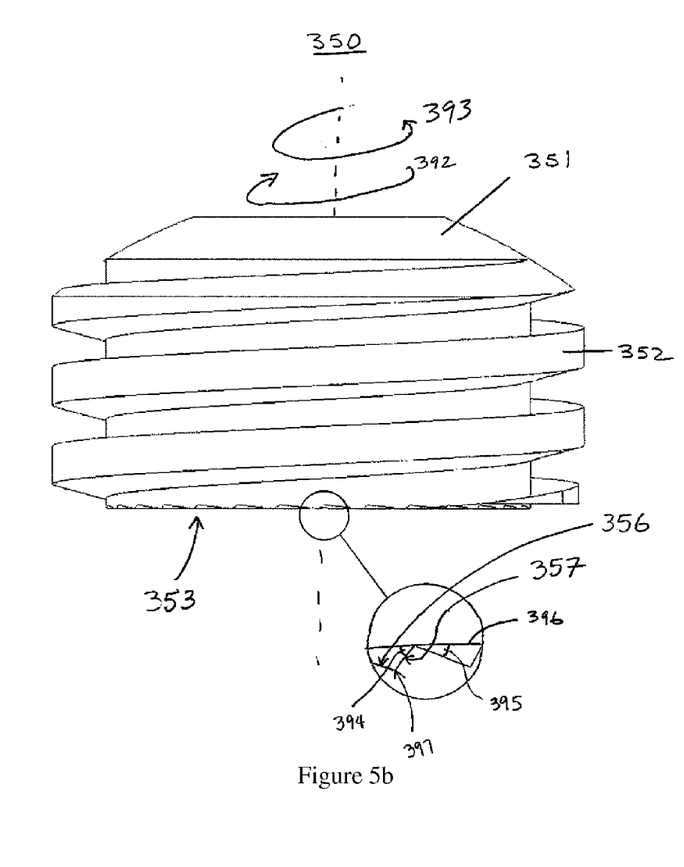
Figure 6A:
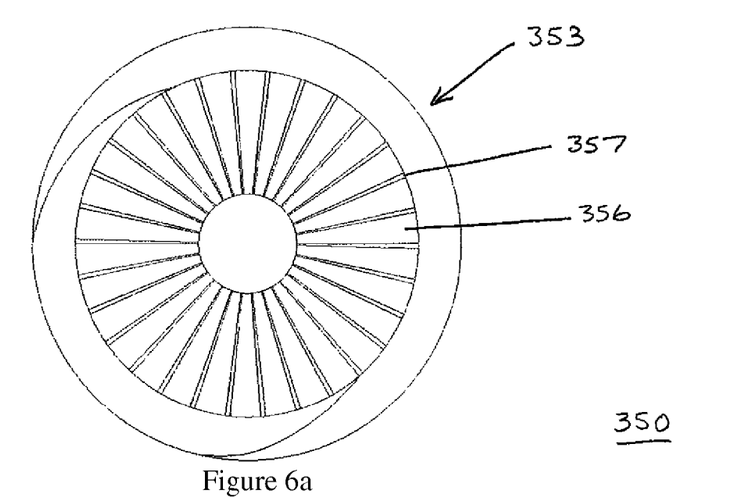
FIG. 6a includes an inferior view of a set screw and FIG. 6b includes a superior view of the set screw and FIG. 6c includes a cross-sectional view of the set screw in an embodiment of the invention.
Figure 6B:
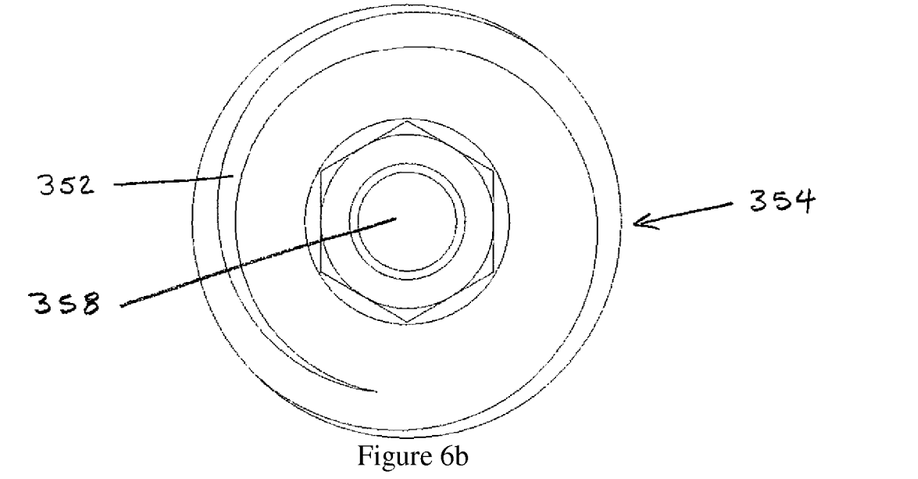
Figure 6C:
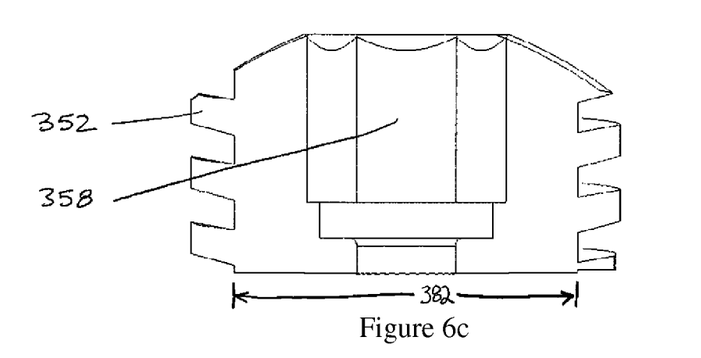

As seen in FIGS. 5 and 6, assembly 301 includes set screw 350 to close open slot 302, stabilize linkage 330, and fixedly couple to detent plate 335 when rotated in tightening direction 392 (and decouple from detent plate 335 when rotated in loosening direction 393). Set screw 350 has inferior set screw face 353 including a radially disposed plurality of ridges complimentary to the plurality of ridges included on detent plate 335. One particular representative ridge is discussed for purposes of simplicity. To that end, one such ridge on set screw face 353 includes resist face 357 formed at acute angle 394, with respect to inferior set screw face plane 396, and advance face 356 formed at acute angle 395, with respect to inferior set screw face plane 396, which is smaller and flatter than angle 394.

Thus, when set screw 350 is forced in tightening direction 392 in certain situations such as, for example, while set screw inferior face 353 initially contacts detent plate superior face 343, the ridges of set screw 350 advance in tightening direction 392 skipping intermittently across, with limited resistance, the ridges of detent plate 335.

Also, consider the situation where, for example, set screw inferior face 353 is already in contact with detent plate superior face 343 after full deployment in a patient and with set screw 350 being fully tightened against detent plate 335. In that situation, when set screw inferior face 353 is forced in loosening direction 393 the resist faces 337, 357 are mated and the ridges on set screw 350 are halted to prevent loosening of set screw 350 and consequent destabilization of linkage 330. The phrase "forced in loosening direction" generally means a force is applied in the loosening direction. The phrase does not necessarily say any resultant motion or rotation occurs. Also, such forces may occur from general movements made by the patient, by the surgeon, and the like.

In other words, detent plate 335 may be used to mechanically resist or arrest the rotation of a wheel, axle, or spindle such as ridged inferior set screw face 353. The ridges of detent face 343 can be used to intentionally divide rotation of set screw 350 into discrete increments and/or to simply arrest rotation of set screw 350 in a loosening direction 393. The resist faces 337, 357 operate to resist loosening of set screw 350 once the set screw is tightened to detent plate 335. The use of "advance" faces 336, 356 helps set screw 350 "advance" while tightening to detent plate 335. Thus, in one embodiment the advance faces are angled so that the wheel of ridges on set screw 350 rotates easily in direction 392, as tip 397 easily lifts or is pushed out of trough 398. Following this, tip 397 advances into the next notch on the detent plate as the ridged wheel of set screw 350 continues rotating. Angles 339, 395 may range in different embodiments to include 5, 10, 15, 20, 25, 30, 35, 40, 45, 50, 55, 60 degrees and so on. For example, angles 339, 395 may each be less than 15 degrees. As another example, angles 339, 395 may each be 5 degrees or less.

In contrast, angles 338, 394 are more severe (i.e., less flat) and may range in different embodiments to include 15, 20, 25, 30, 35, 40, 45, 50, 55, 60, 65, 70, 75, 80, 85, and 90 degrees so tip 397 cannot be easily pushed up or out of trough 398 if the ridged wheel of set screw 350 is forced (although not necessarily moved) in the loosening direction 393. For example, angles 338, 394 may each be more than 15 degrees. As another example, angles 338, 394 may each be 30 degrees or more.

As used herein, an orthopedic set screw is a type of orthopedic screw generally used to secure a fixation linkage within a holder. The set screw may be fully threaded and may or may not have an external head. Set screw 350 may be inserted into tulip 305 using any number of drivers such as an internal Hex, Allen, slot, Torx, star or Phillips key or driver. Orthopedic set screws may pass through a threaded hole in an outer object, such as a tulip, and be tightened against an inner object, such as an intervertebral fixation rod, to prevent the inner object from moving relative to the outer object. The orthopedic set screw exerts compressional or clamping force through the bottom tip of the set screw.

In an embodiment, detent plate 335 includes inferior detent face 344 including concave portion 338' contoured to complement an outer profile of linkage 330. Such an outer profile may be spherical but other profiles (e.g., elliptical, square, flat, oval) are possible.

In an embodiment detent plate 335 and its ridges, used to couple to ridges on set screw 350, are monolithic. In other words, the ridges of face 343 may be formed to plate 335 without seams and formed from a single material. In other embodiments there may be intervening plates or other materials between plate 335 and ridges 336, 337. Also, in an embodiment set screw 350 and the ridges on face 353 are monolithic. In other embodiments there may be intervening plates or other materials between set screw 350 and ridges 357, 356.

As seen in FIG. 9, in an embodiment detent plate 335 is permanently coupled to set screw 350 via pivot member 340 so detent plate 335 can pivot about (see arrows 377, 378) set screw 350 when the set screw is not fully tightened against the detent plate. This rotation is possible because space 379 exists between plate 335 and screw 350 when the two are not fully tightened against one another (yet still loosely coupled to one another via pivot 340). However, when the two are fully tightened against one another space 379 is removed as face 343 fully mates to face 353. By permanently coupled, a person of ordinary skill in the art will appreciate that using extraordinary means the detent plate and set screw can be separated. However, a "permanently coupled" embodiment in typical clinical situations may allow a surgeon to avoid having to individually place the detent plate and set screw into the tulip. Instead, he or she may place the detent plate and set screw into the tulip as a permanently coupled unit. This facilitates ease of handling in the surgical environment. Also, the pivot member allows for orienting the detent plate as needed to couple to the linkage and also allows the set screw to then tightly couple to the detent plate.

In an embodiment set screw inferior face includes maximum breadth 382 less than maximum breadth 381 of detent plate superior face. In an embodiment, detent plate maximum breadth 381 may be generally 9.5, 9.6, 9.7, 9.8, 9.9, 1.0, 1.1, 1.2, 1.3, 1.4, 1.5 mm and the like and minimum breadth 386 may be generally 5.0, 5.1, 5.2, 5.3, 5.4, 5.5, 5.6, 5.7, 5.8, 5.9, 6.0 mm and the like. In an embodiment, after set screw 350 is fully tightened against detent plate 335, and the set screw is forced in loosening direction 393 (but not necessarily moved in direction 393), side face 342 of detent plate 335 abuts one of the tulip side walls defined by wall edges 315, 316, 317, 318 to halt rotation of detent plate 335 and prevent loosening of set screw 350 and destabilization of linkage 330.

In an embodiment, set screw threads 352 mate with corresponding threads 383 included in walls of tulip 305. In an embodiment, when set screw 350 is fully tightened against detent plate 335 and the set screw is forced in loosening direction 393, rotational movement of linkage 330, about longitudinal axis 384 of anchor element 310, is halted by a side wall of tulip 305 and translational movement of linkage 330 along horizontal axis 385, perpendicular to longitudinal axis 384, is halted by detent plate 335.

Thus, some embodiments provide that when a set screw is fully tightened against a detent plate, pluralities of ridges on opposing faces of the detent plate and set screw cooperate by providing catches to prevent loosening of the set screw until a loosening force surpassing a first threshold is applied to the set screw. That is to say, in an embodiment the detent plate is not irreversible. Once the set screw is fully tightened to the detent plate, the set screw can be loosened. However, the detent plate makes such loosening more difficult and less likely to inadvertently occur during, for example, typical movements by the patient once the implant has been installed.

Figure 7:
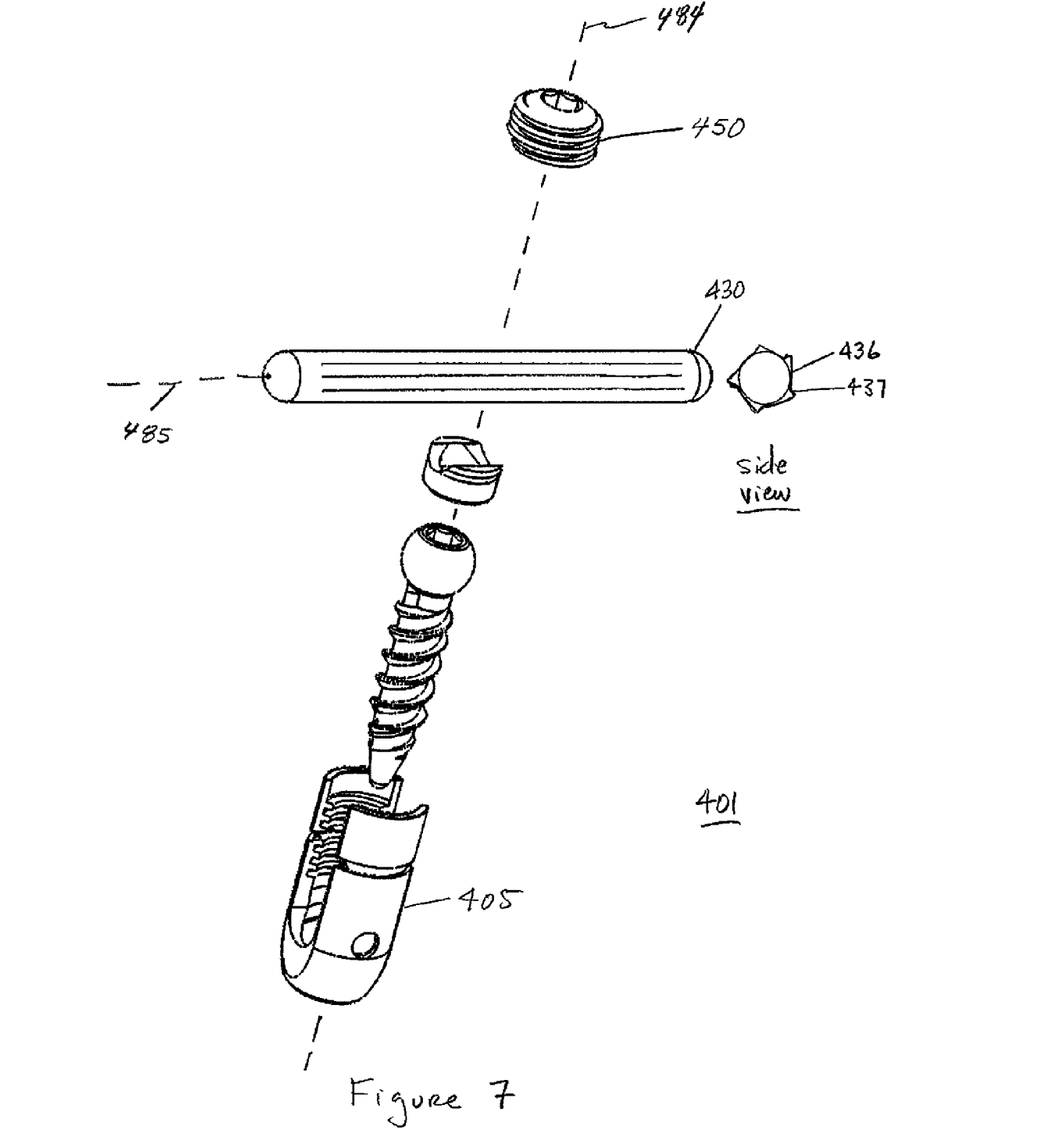
FIG. 7 includes an assembly in an embodiment of the invention.

FIG. 7 includes an assembly in an embodiment of the invention. Assembly 401 includes no detent plate or pivot member such as shown in FIG. 1. Instead, linkage 430 may include longitudinal ridges. Taking one such ridge as an example, the ridge includes resist face 437 and advance face 436. Principles of operation for assembly 401 resemble those for assembly 301. However, set screw 450 mates directly to linkage 430. Set screw 350 (FIG. 5) may be substituted for set screw 450. Thus, during tightening advance faces 436, 356 may cooperate to allow tightening without a great deal of rotational force. However, resist faces 357, 437 may cooperate to resist, entirely or substantially, loosening of set screw 450 within tulip 405, thereby stabilizing linkage 430. The outer profile for linkage 430 may be spherical but other profiles (e.g., elliptical, flat, square, oval) are possible.

Figure 8:
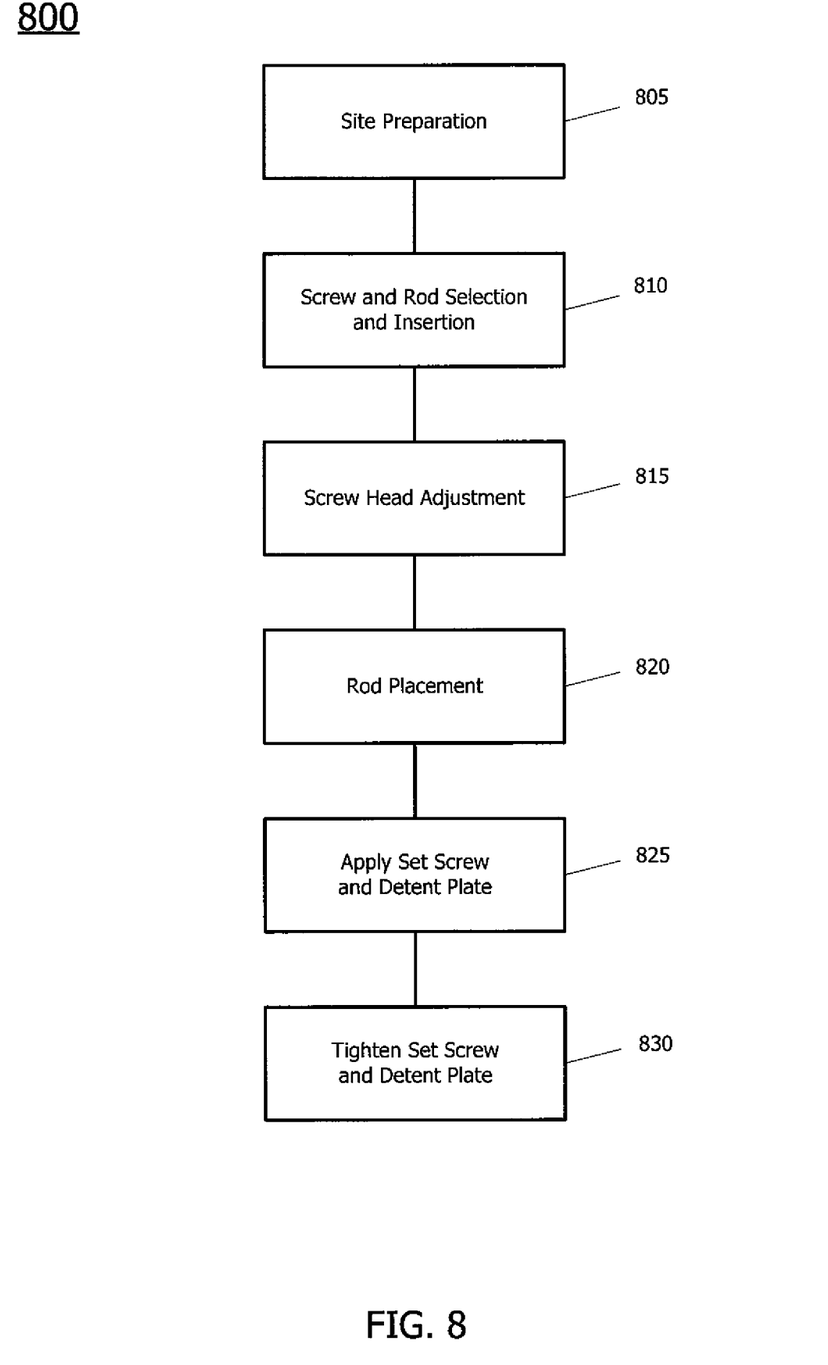
FIG. 8 includes a schematic flow chart for a method in an embodiment of the invention.

Embodiments of methods for employing devices described herein are now addressed. In FIG. 8, method 800 includes block 805 where site preparation occurs. Specifically, after exposing pedicle screw entry points, a starting hole may be started with a burr, rongeur or bone awl. The awl may insert to a depth of 20 millimeters. Fluoroscopy may be utilized by the surgeon to allow for more accurate placement of pedicle screws. Alternatively, plain x-ray may be utilized to visualize the appropriate trajectory. The surgeon may enter the pedicle with the pedicle probe. The angled or straight probe may be utilized at the surgeon's discretion. A smaller diameter probe may be made available for smaller or more difficult pedicles. The probe should be rotated with entry to allow for the path of least resistance and to reduce stress on the probe. Calibration on the shaft is utilized to choose the appropriate length screw. Depth should be measured from the initial entry point. A ball tipped probe may then be placed in the pedicle hole to aid in checking for intact walls and determining if the anterior cortex is intact at full depth. Depending on bone density at the insertion sit; a tap may be utilized to ease the insertion of the screw.

In block 810, screw selection is made. Screw diameter options may include 4.5, 5.5, 6.5, 7.5, 8.5 mm and the like. All screw diameters may be available in a tray. The screw may then be placed on the driver, held securely by interference fit, and through a tulip. The driver may be ratcheted for clockwise or counter clockwise rotation or fixed position. The screw and tulip may then be inserted until the bottom of the screw head is flush with the bony cortex. Alternatively, the screw may be allowed to seat slightly higher to aid in alignment for rod placement if the surgeon chooses. The driver may disengage by simply pulling it directly out of the screw hex receiving point. Rod selection may then be made. Both pre-bent and straight rods may be available. Rod lengths may include, for example, 35 mm, 40 mm and so on with 10 mm increments up to, for example, 150 mm in a standard set.

In block 815, the screw head may remain in position after adjustment. The screw heads and tulips may be aligned with a tulip positioner to allow for easy rod placement. Screw heads and tulips may be angled to allow for easier rod placement and for future screw removal if necessary.

In block 820, the rod may be clamped by a rod holder and seated into the screw heads. If necessary, the assembly may come with a reduction screw option that includes a tulip with extended tabs or side walls to facilitate access (e.g., move tissue aside) to the inside of the tulip near the anchor or screw head. These extended tabs should allow for easy capture of the rods if the surgeon so chooses. The extended tabs may be configured to "breakaway" when the surgeon has completed device insertion and wishes to minimize the profile of the hardware to remain in the patient.

In block 825, a set screw and detent plate, such as the embodiments described herein in conjunction with FIGS. 1-7 and 9, may be inserted into the tulip. The set screw and detent plate may be inserted separately into the tulip. However, the set screw and detent plate may already be coupled via a pivot member and the entire set screw—pivot member—detent plate combination may be placed in the tulip at one time. The set screw may be rotated counterclockwise initially to allow for seating within the threads of the tulip. The set screw may then be advanced down to the rod by rotating the set screw clockwise. When the set screw and detent plate are provisionally seated, the rod placement within the screws can be adjusted prior to final seating. Once seated, before final tightening, the rod may be lightly held in position to aid in the prevention of further rod movement.

In block 830, the set screw and detent plate may be fully tightened to the rod using an anti-torque device which is seated on the rod. The insertion driver may continue to rotate, and the screw may advance a bit more as the ridges on the set screw advance over the complementary ridges on the detent plate. This may occur until the set screw is fully tightened to the detent plate. A torque driver may be used that has a breakaway feature which occurs at, for example, 12 N-m of torque. The screw may be advanced until a click is heard which indicates the "breakaway" occurred. The set screw and detent plate may then be fully seated.

Embodiments herein have focused on spine fixation systems but embodiments are not so limited and may have utility in more general orthopedic fixation systems used in, for example, fixation of fractured long bones, limbs, and the like.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An orthopedic linkage securing anchor assembly, wherein the anchor assembly comprises:
    an anchor element to attach to a bone;
    a tulip, to couple to the anchor element, having an open slot to receive a linkage, the tulip including at least two side walls to define at least a portion of the open slot;
    a detent plate to couple to the linkage, wherein the detent plate has a superior detent face including a radially disposed plurality of first ridges, each first ridge including a first resist face formed at an acute angle, with respect to the superior detent face, and a first advance face formed at another acute angle, with respect to the superior detent face, that is smaller and flatter than the acute angle of the first resist face;

a set screw to close the open slot and stabilize the linkage, wherein the set screw has an inferior set screw face including a radially disposed plurality of second ridges complimentary to the plurality of first ridges, each second ridge including a second resist face formed at an acute angle, with respect to the inferior set screw face, and a second advance face formed at another acute angle, with respect to the inferior set screw face, that is smaller and flatter than the acute angle of the second resist face;

wherein in a first position when the set screw is forced in a tightening direction, while the set screw inferior face contacts the detent plate superior face, the second plurality of ridges advances in the tightening direction and is not completely halted by the first plurality of ridges;

wherein in a second position when the set screw inferior face, already in contact with the detent plate superior face with the set screw and already fully tightened against the detent plate, is forced in a loosening direction the first and second resist faces are mated and the second plurality of ridges is halted by the first plurality of ridges to prevent loosening of the set screw;

wherein the acute angle and the another acute angle of the first ridge are interior angles for a triangle defined by the superior detent face and the first resist and advance faces;

wherein the plurality of second ridges fixedly couple to the plurality of first ridges when the set screw is rotated in the tightening direction and decouple from the plurality of first ridges when the set screw is rotated in the loosening direction;

wherein (a) the detent plate is fixedly coupled to the set screw via a pivot member, and (b) the assembly includes a first unoccupied space between the pluralities of first and second ridges when the set screw is not fully tightened against the detent plate, and wherein when the set screw is fully tightened against the detent plate the first space is removed; wherein the pivot member directly connects to the set screw and the detent plate such that the detent plate rotates about the pivot member while remaining fixedly coupled to the set screw.

2. The assembly of claim 1, wherein the detent plate is permanently coupled, and not removably coupled, to the set screw via the pivot member so the detent plate can pivot about the set screw.

3. The assembly of claim 2, wherein the detent plate is permanently coupled to the set screw via the pivot member so when the detent plate, pivot member, and set screw are removed from the assembly the detent plate, pivot member, and set screw are still coupled to one another.

4. The assembly of claim 1, wherein the detent plate includes an inferior detent face including a concave portion contoured to complement an outer profile of the linkage.

5. The assembly of claim 1, wherein (a) the detent plate and the plurality of first ridges are monolithic and (b) the set screw and the plurality of second ridges are monolithic.

6. The assembly of claim 1, wherein (a) the detent plate superior face outer profile is non-circular and (b) the set screw inferior face includes a maximum breadth less than a maximum breadth of the detent plate superior face.

7. The assembly of claim 1, wherein when the (a) set screw inferior face contacts the detent plate superior face with the set screw fully tightened against the detent plate, and (b) the set screw is forced in the loosening direction, (c) a side face of the detent plate passes completely through an outermost edge of a channel that completely traverses the tulip from one outermost edge of the tulip to an opposite outermost edge of the tulip.

8. The assembly of claim 1, wherein the set screw includes threads to compatibly mate with corresponding threads included in the at least two side walls of the tulip.

9. The assembly of claim 1, wherein (a) when the set screw is fully tightened against the detent plate, and the set screw is forced in the loosening direction (b) rotational movement of the linkage, about the longitudinal axis of the anchor element, is halted by at least one of the at least two side walls of the tulip and translational movement of the linkage, perpendicular to the longitudinal axis, is halted by the detent plate.

10. The assembly of claim 1, wherein when the set screw is fully tightened against the detent plate the pluralities of first and second ridges comprise catches to prevent loosening of the set screw until a loosening force surpassing a first threshold is applied to the set screw.

11. The assembly of claim 1 wherein (a) the linkage includes an intervertebral fixation rod, (b) the anchor element includes a bone screw, and (c) the acute angles of the first and second advance faces are both less than fifteen degrees and the acute angles of the first and second resist faces are both more than fifteen degrees.

12. The assembly of claim 1:
wherein the detent plate includes an inferior detent face including a concave portion contoured to complement a circular outer profile of the linkage.

13. An orthopedic linkage securing anchor assembly, wherein the anchor assembly comprises:
an anchor element to attach to a bone;
a tulip, to couple to the anchor element, having an open slot to receive a linkage, the tulip including at least two side walls to define at least a portion of the open slot;
a detent plate to couple to the linkage, wherein the detent plate has a superior detent face including a radially disposed plurality of first ridges, each first ridge including a first resist face formed at an acute angle, with respect to the superior detent face, and a first advance face formed at another acute angle, with respect to the superior detent face, that is smaller and flatter than the acute angle of the first resist face;
a set screw to close the open slot, stabilize the linkage, and fixedly couple to the detent plate when rotated in a tightening direction and to decouple from the detent plate when rotated in a loosening direction, wherein the set screw has an inferior set screw face including a radially disposed plurality of second ridges complimentary to the plurality of first ridges, each second ridge including a second resist face formed at an acute angle, with respect to the inferior set screw face, and a second advance face formed at another acute angle, with respect to the inferior set screw face, that is smaller and flatter than the acute angle of the second resist face;
wherein in a first position when the set screw is forced in the tightening direction, while the set screw inferior face contacts the detent plate superior face, the second plurality of ridges advances in the tightening direction and is not completely halted by the first plurality of ridges;
wherein in a second position when the set screw inferior face, already in contact with the detent plate superior face with the set screw already fully tightened against the detent plate, is forced in the loosening direction the first and second resist faces are mated and the second plurality of ridges is halted by the first plurality of ridges to prevent loosening of the set screw wherein (a) the detent plate is fixedly coupled to the set screw via a pivot member, and (b) the assembly includes a first unoccupied space between the pluralities of first and second ridges when (b)(i) the set screw is not fully tightened against the detent plate, (b)(ii) the detent plate is already fixedly coupled to the set screw, and (b)(iii) the set screw directly connects to the pivot member and the pivot member directly connects to the detent plate such that the detent plate rotates about the pivot member and set screw while remaining fixedly coupled to the set screw, and when the set screw is fully tightened against the detent plate the first space is removed.

14. The assembly of claim 13, wherein the detent plate is permanently coupled to the set screw via the pivot member so when the detent plate, pivot member, and set screw are removed from the assembly the detent plate, pivot member, and set screw are still coupled to one another while simultaneously the first unoccupied space exists and the detent plate remains permanently coupled to the set screw.

* * * * *